United States Patent [19]

Eratt et al.

[11] Patent Number: 4,870,014
[45] Date of Patent: Sep. 26, 1989

[54] CLONING OF THERMOLABILE GLUCOAMYLASE GENE INTO SACCHAROMYCES CEREVISIAE

[75] Inventors: Judy A. Eratt; Anwar Nasim, both of Ottawa, Canada

[73] Assignee: Canadian Patents and Development Ltd., Ottawa, Canada

[21] Appl. No.: 776,370

[22] Filed: Sep. 16, 1985

[51] Int. Cl.$^4$ .................... C12N 15/00; C12N 1/20; C12N 5/00

[52] U.S. Cl. .................... 435/172.3; 435/91; 435/322; 435/255; 435/256; 435/202; 435/203; 435/204; 435/205; 536/27; 935/28; 935/60; 935/69

[58] Field of Search .................... 435/172.3, 91, 202, 435/203, 204, 205, 940, 942, 320, 255, 256; 935/60, 28, 69; 536/27

[56] References Cited

PUBLICATIONS

Yamashita I. and S. Fujui; Molecular Cloning of a Glucoamylase Producing Gene in the Yeast *Saccharomycej*; Agric. Biol. Chem. 47 (11), pp. 2689–2692, (1983).

Yamashita et al., Nucleotide Sequence of the Extracellular Glucoamylase Gene STAI in the Yeast S. diastaticus; J. Bacteriol. 161(2), pp. 567–573, (1985a).

Yamashita et al., Polymorphic Extracellular Glucoamylase Genes and their Evolutionary Origin in the Yeast *S. diastaticus*; J. Bacteriol. 161(2), pp. 574–582, (1985b).

Meaden P. et al., A DEX Gene Conferring Production of Extracellular Amyloglycosidase on Yeast; Gene 34, 325–334, (1985).

E. M. Southern, Detection of . . . Electrophoresis, J. Mol. Biol, (1975), 98, 503–507.

K. Nasmyth & S. Reid, Isolation of . . . cell–cycle gene, Proc. Natl. Acad. Sci. USA vol. 77, No. 4, 2119–2123, Apr. 1980.

J. D. Beggs, Transformation of . . . plasmid, Nature, vol. 275, Sep. 14, 1978, 104–109.

D. Cryer, R. Eccleshall, J. Marmur, Isolation of Yeast DNA, Chap. 3, Dept. of Biochemistry, Albert Einstein College of Medicine, New York, 39–44.

G. Godson, D. Vapnek, A Simple Method . . . Supercoiled DNA, Biochimica et Biophysics Acta, 299 (1973), 516–520.

*Primary Examiner*—Robin Teskin
*Attorney, Agent, or Firm*—Alan A. Thomson

[57] ABSTRACT

This inverntion concerns a glycoamylase gene cloned into the yeast *Saccharomyces cerevisiae*, method for cloning such a gene into such yeasts and cloning vehicles containing such a gene, suitable for use in *Saccharomyces cerevisiae*. Yeast containing a glucoamylase gene are of potential use in the brewing industry.

9 Claims, 4 Drawing Sheets

CLONING OF THERMOLABILE GLUCOAMYLASE GENE INTO SACCHAROMYCES CEREVISIAE

BACKGROUND OF THE INVENTION

This invention is concerned with the introduction of a gene coding for a thermolabile glucoamylase when expressed in the organism into which they have been cloned.

S. cerevisiae, the yeast most commonly used in fermentation, is only capable of fermenting glucose, sucrose, fructose, maltose and maltotriose. Larger sugars and starch cannot be utilized by this yeast and, therefore, they must be hydrolyzed, usually by the use of enzymes and/or heat before fermentation of these more complex substrates can proceed. U.S. Pat. No. 4,469,791 (inventors: C. A. Colson et al, issued Sept. 4, 1984) discloses the cloning of genes coding for thermostable glucoamylases in bacteria. Thermostable glucoamylases are particularly useful in the production of materials such as high fructose corn syrup.

The nearest prior art to this invention concerns the introduction of thermostable glucocamylase genes from Saccharomyces diastaticus into Saccharomyces cerevisiase. I. Yamashita and S. Fukui in Agric. Biol. Chem. 47(11), 2689-2692 (1983) employed a STA1 gene and P. Meaden et al in Gene 34, 325-334 (1985) employed a DEX1 gene.

There is a need for a thermolabile glucoamylase in yeast fermentation of complex carbohydrates in the brewing industry. The brewing industry commonly pasteurizes beer and the pasteurization step can therefore also be used to inactivate thermolabile glucoamylases which have been previously added being particularly useful in the production of light beers.

It is an object of the invention to provide a gene coding for a glucoamylase thermolabile when expressed by a microorganism into which it has been cloned.

SUMMARY OF THE INVENTION

We have found that the lack of thermolabile glucoamylase activity, especially in a yeast of the Saccharomyces cerevisiae type, can be overcome using a method of producing a cloning vehicle containing a gene coding for glucoamylase, thermolabile when said gene is subsequently expressed by a selected microorganism.

Such a method comprises:

(a) isolating genomic DNA from an organism, such as a selected strain of Saccharomyces diastaticus, containing said gene;

(b) digesting said genomic DNA with a restriction endonuclease selected to yield DNA fragments containing complete copies of said gene;

(c) selecting DNA fragments containing complete copies of said gene: this may comprise separating the DNA fragments resulting from step (b) on a sucrose gradient between 10% and 30% w/v and selecting DNA fragments between 5 kb and 15 kb; and (d) ligating the product of step (c) into a selected cloning vehicle, for example a cloning vehicle of the YEp13 type to yield a cloning vehicle containing said gene.

In this way cloning vehicles, suitable for insertion into a selected microorganism such as a yeast of the Saccharomyces cerevisiae type, containing a gene coding for glucoamylase thermolabile when said gene is expressed by such a microorganism, can be produced. The gene is preferably derived from a yeast of the Saccharomyces diastaticus type.

A gene coding for a glucoamylase, thermolabile when said gene is expressed by a selected microorganism, especially a yeast of the Saccharomyces cerevisiae type, may be cloned by following step (a) to (d) outlined above with;

(e) transforming such a microorganism with the cloning vehicle resulting from step (d); and (f) selecting transformants resulting from step (e) which express the glucoamylase gene.

Step (d) above may be preceded by:

(i) transforming E. coli with the cloning vehicle resulting from step (d);

(ii) selecting transformants resulting from step (i); and (iii) isolating an amplified form of the product.

In this way transformants containing a gene coding for a glucoamylase thermolabile when expressed by such a transformant may be produced.

Thermolabile glucoamylase may be produced by culturing such transformants under conditions selected to yield thermolabile glucoamylase which may be used, for example, to clarify starch-containing liquids by testing such a liquid with the enzyme until clear. This may be followed by heating to inactivate the enzyme, a procedure of particular potential in the brewing industry.

DETAILED DESCRIPTION OF THE INVENTION

Example

Figure 1:
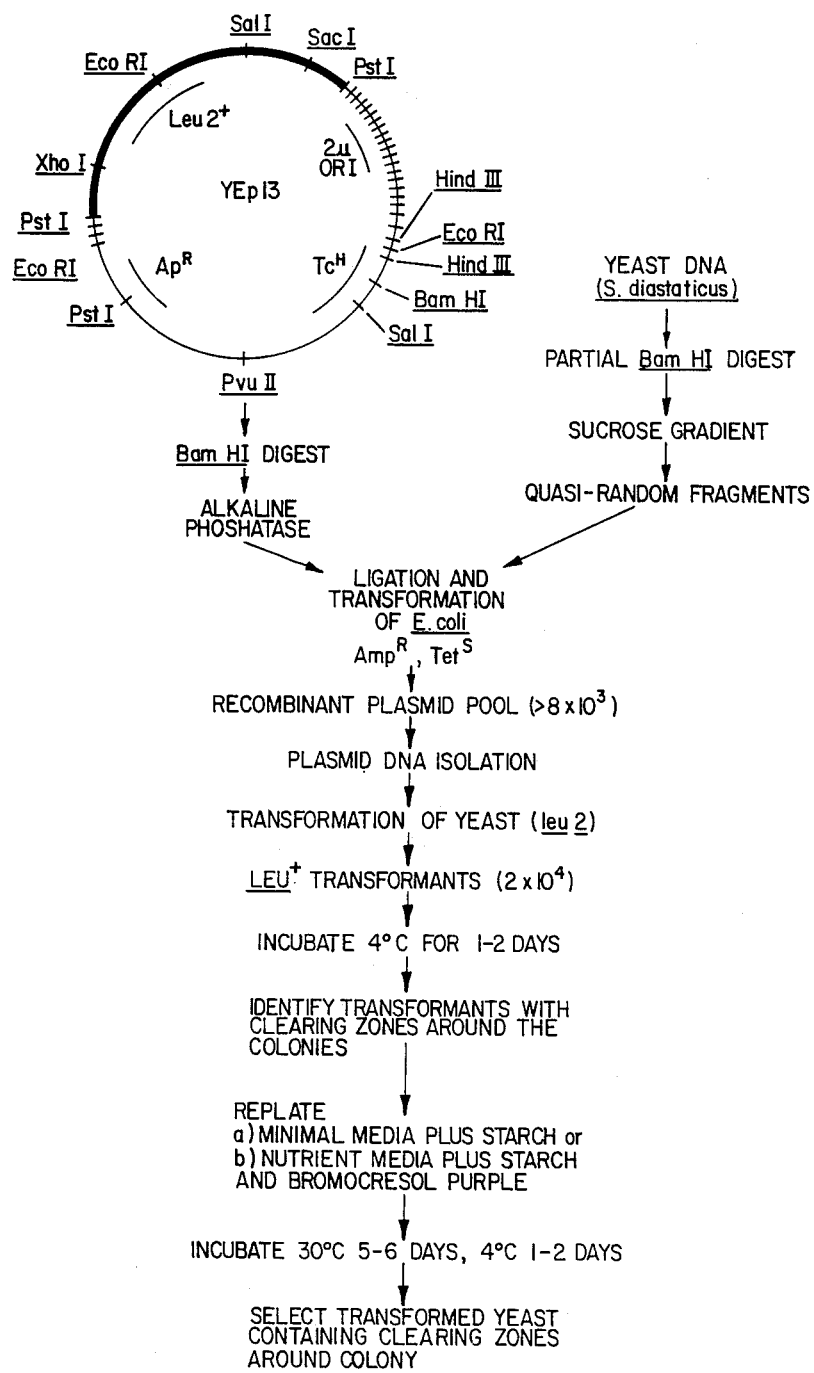
FIG. 1 illustrates the methodology employed in a preferred embodiment of the invention.

The basic procedure employed is laid out in schematic form in FIG. 1.

Organisms, DNAs and Enzymes. The following strains were used: S. diastaticus J3120-13C ATCC 62988 mat a, DEX1, DEX2, STA3), S. cerevisiae LL20 ATCC 62995 (mat α, leu2-3, leu2-11, his3-11, his3-15) and Escherichia coli RR1 and RR1 containing the plasmid YEp13. Plasmid DNA was prepared by the method described by G. N. Godson and D. Vapnek in Biochim. Biophys. Acta 299, 516-520 (1973) with minor modifications. Yeast DNA was prepared from S. diastaticus J3120-13C using the standard procedures of D. R. Cryer et al in "Methods of Cell Biology", Vol. 12, D. M. Prescott (ed.) Academic Press (1975). All restrictions enzymes, alkaline phosphatase and T4 DNA ligase were standard commercially available items.

Construction of a Pool of Yeast DNA Sequences in YEp13. Yeast DNA from S. diastaticus J3120-13C, was partially cleaved with BamHI and the resulting fragments were separated according to size on a sucrose gradient (10%-30%). Fragments ranging in size between 5 and 15 kb were ligated to YEp13, which had been digested with BamHI and calf intestinal alkaline phosphatase (the respective DNA concentration were 0.4 and 0.2 μg/ml). After ligation, the DNA was used to transform *E. coli* RR1 to ampicilin resistance (Amp$^R$). Approximately $1.2 \times 10^3$ Amp$^R$ colonies were selected, of which 85% were tetracycline sensitive (Tet$^S$). The transformed colonies were pooled and plasmid DNA was isolated to yield the *S. diastaticus* yeast bank.

Yeast transformation. The standard yeast transformation procedure described by J. D. Beggs, Nature, 275, 104–109, (1978) was used, with minor modifications, to transform *S. cerevisiae* LL20 with the *S. diastaticus* plasmid bank. In order to screen the transformants for the presence of glucoamylase activity the following method was developed. The protoplasts were regenerated on a minimal medium containing 1% (w/v) dextrose, 2% (w/v) starch, 20 μg/ml histidine and 1.2M sorbitol in the overlay agar. After the protoplasts had regenerated the plates were placed at 4° C. for 2-3 days to allow the starch to precipitate. The transformants were then screened for clearing zones around the colonies where starch hydrolysis had occurred.

Cloning of a Glucoamylase Gene by Complementation in Yeast. The yeast strain *S. cerevisiae*, LL20, was transformed with the *S. diastaticus* plasmid bank. LEU+ transformants were selected by plating the transformation mixture on minimal medium containing histidine and starch. Of the $2 \times 10^4$ transformants obtained 9 were selected, which had a slight clearing zone around the colonies, following incubation at 4° C. for 2-3 days. Six of the original nine showed glucoamylase activity upon subculturing to selective media, representing 0.03% of the total LEU+ transformants.

Recovery of the Plasmids from Yeast Transformants. Mini-plasmid preparations were made from the six yeasts transformants showing glucoamylase activity using the method of K. A. Nasmyth and S. L. Reed, Proc. Natl. Acad. Sci. U.S.A. 77, 2119–2123 (1980). This DNA was used to transform *E. coli* RR1. The recloned plasmids were isolated and used to transform LL20. Each plasmid produced approximately the same number of transformants (300 per μg of DNA). All transformants from the six plasmid samples:

(YEp(DEX)3, YEp(DEX)4, YEp(DEX)5, YEp(DEX)6, YEp(DEX)7 and YEp(DEX)9) exhibited glucoamylase activity.

Restriction map of cloned glucoamylase fragments

To determine the restriction map, of the inserts, the 6 recombinant plasmids were first digested to completion with BamHI. It was ascertained that the six recombinant plasmids contained the same size of insert (approximately 3.9 kb). These BamHI samples were then digested to completion with: EcoRI, HindIII, SalI, PstI, KpnI or PvuII and SalI together with KpnI, PstI or EcoRI to determine the restriction map of the insert (from YEp(DEX)4).

Following restriction hydrolysis, the DNA fragments were separated using 0.7% horizontal agarose gels in Tris/acetate/EDTA buffer, pH 8.1 (60 mM Tris, 5 mM sodium acetate and 1 mM EDTA). The DNA was then transferred to nitrocellulose as described by E. M. Southern in J. Mol. Biol. 98, 503–517 (1975). The cloned glucoamylase fragment was labelled by nick translation using $^{32}$P-dATP and used to probe for homologous sequences. Hybridization was done under stringent conditions in six fold concentrated SSC, 0.1% SDS and five fold concentrated Denhardt's solution at 65° C. This was followed by washes at 65° C. in six fold concentrated SSC and 0.1% SDS. The nitrocellulose filters were then exposed to Kodak XAR-5[TM] film at −70° C. with Kodak[TM] intensifying screens.

Figure 2:
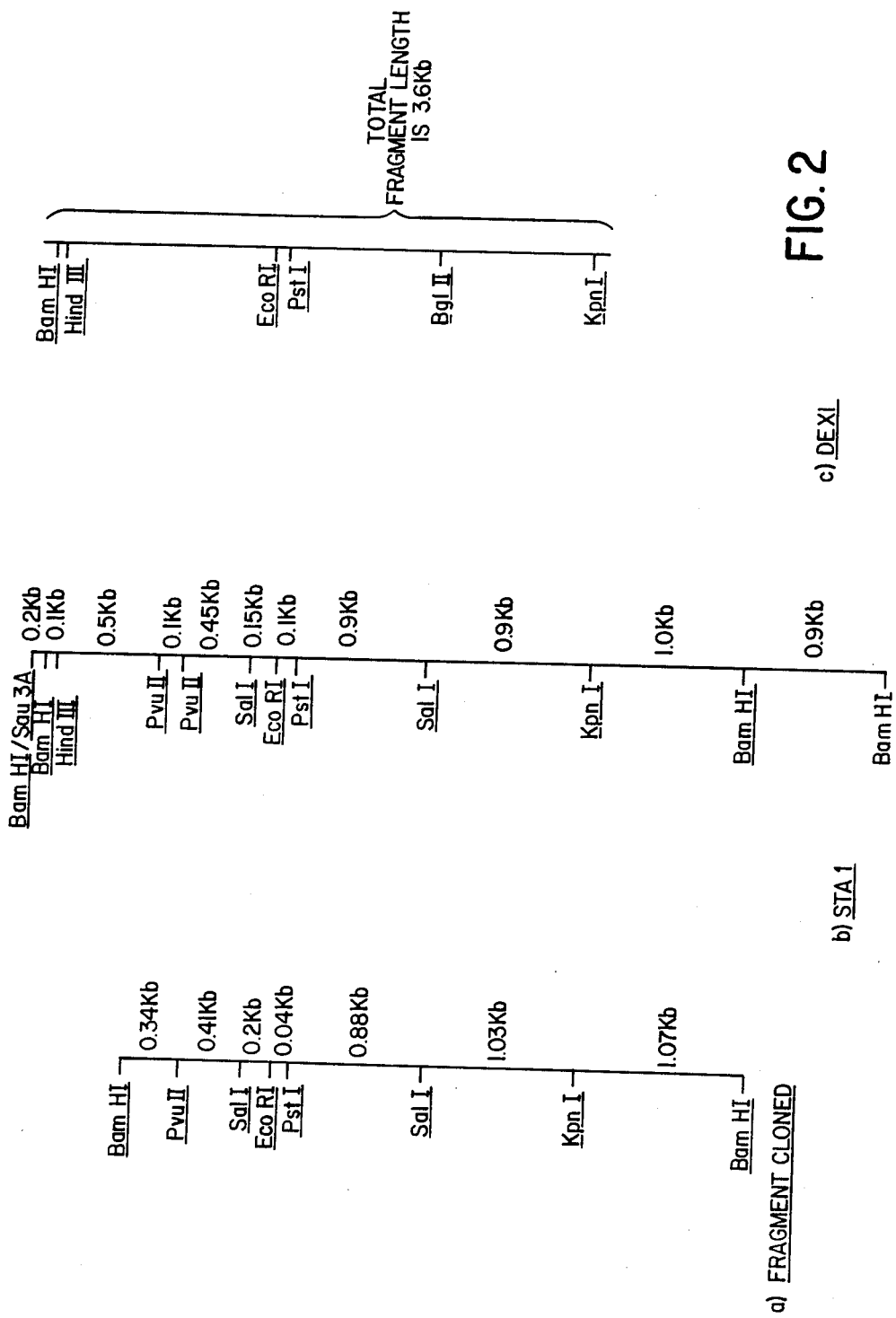
FIG. 2 is a comparison of the restriction map of STA1, DEX1 and the glucoamylase cloned in the preferred embodiment of this invention.

As can be seen from FIG. 2 the glucoamylase gene fragment cloned in this work has a restriction map different from the glucoamylase genes cloned by Yamashita and Fukui (1983, op cit.) and Meaden et al. (1985 op cit.) even though direct comparisons are difficult because many of the restriction enzymes used in making the restriction map differ. Particular points of difference include (1) the BamHI fragment in the prior art fragments is approximately 0.3 to 0.7 kb larger, (2) the prior art fragments both contain HindIII sites, and (3) STA1 contains two PvuII sites.

Determination of Glucoamylase Activity in the Transformed Yeast Cultures.

The transformed yeast cultures were inoculated into 100 ml of minimal media, containing 2% glucose and supplemented with histidine, and were incubated at 30° C. on a rotary shaker for 4 days. These cultures were used to inoculate fresh complete medium (1% yeast extract, 2% peptone) containing 2% starch, at a rate of 1% (v/v). In the complete medium excreted glucoamylase activity was detected in the medium from the transformed yeast strains. On the average the 6 strains produced glucoamylase activity at 7× the basal level of LL20. However, it was still considerably less than the glucoamylase activity found in the medium of the donor strain *S. diastaticus*. Differential growth rate cannot account for the differences in glucoamylase activity. Although J3120-13C did have an increased level of growth when compared to the transformed yeast strains, the difference was only approximately 3 fold.

TABLE 1

| GLUCOAMYLASE ACTIVITY SECRETED BY THE TRANSFORMED YEAST STRAINS | |
|---|---|
| TRANSFORMANT | GLUCOAMYLASE ACTIVITY[a] COMPLETE MEDIA |
| YEp(DEX)3 | 33.4 |
| YEp(DEX)4 | 61.9 |
| YEp(DEX)5 | 25.3 |
| YEp(DEX)6 | 47.7 |
| YEp(DEX)7 | 17.8 |
| YEp(DEX)9 | 33.3 |
| *S. cerevisiae* LL20 | 4.9 |
| *S. diastaticus* (J3120-13C) | 1449.7 |

Figure 3:
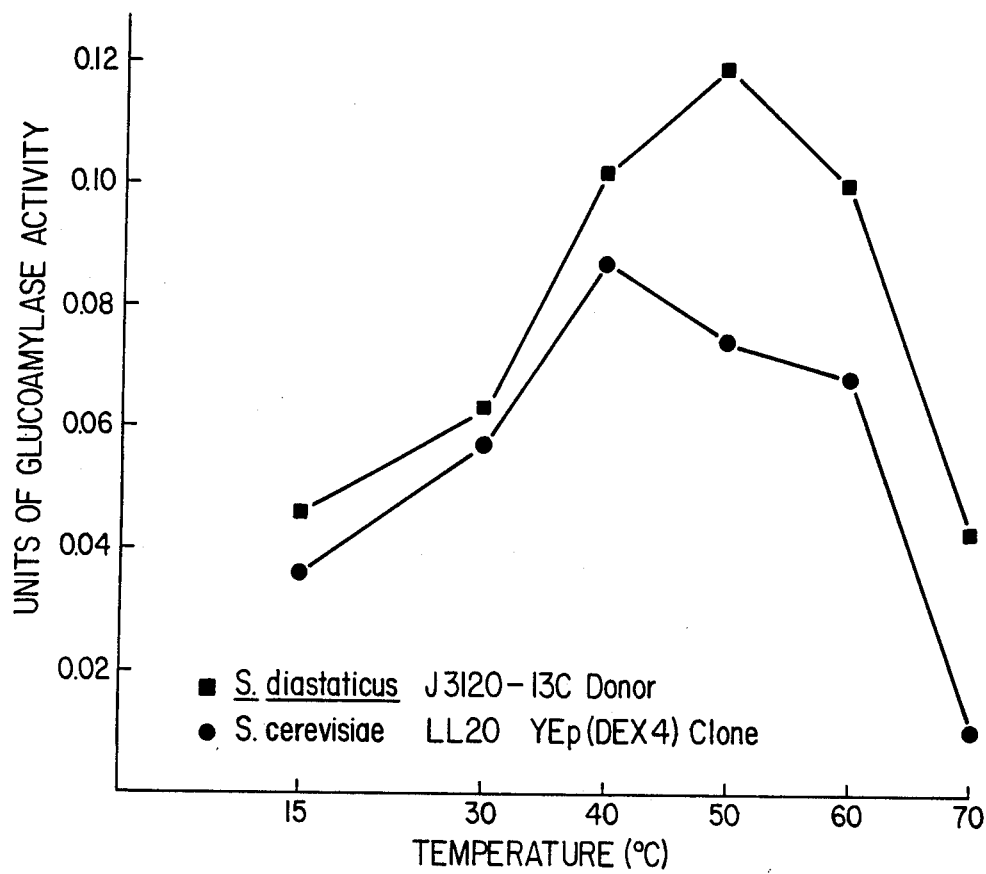
FIG. 3 is a graph of units of glucoamylase activity, where one unit equals the amount of enzyme required to release 1 mg of glucose from starch, in a cell free system, incubated at 30° C. for 1 hour, against temperature when the glucoamylase is produced by S. diastaticus and when it is produced by the transformed S. cerevisiae.
Figure 4:
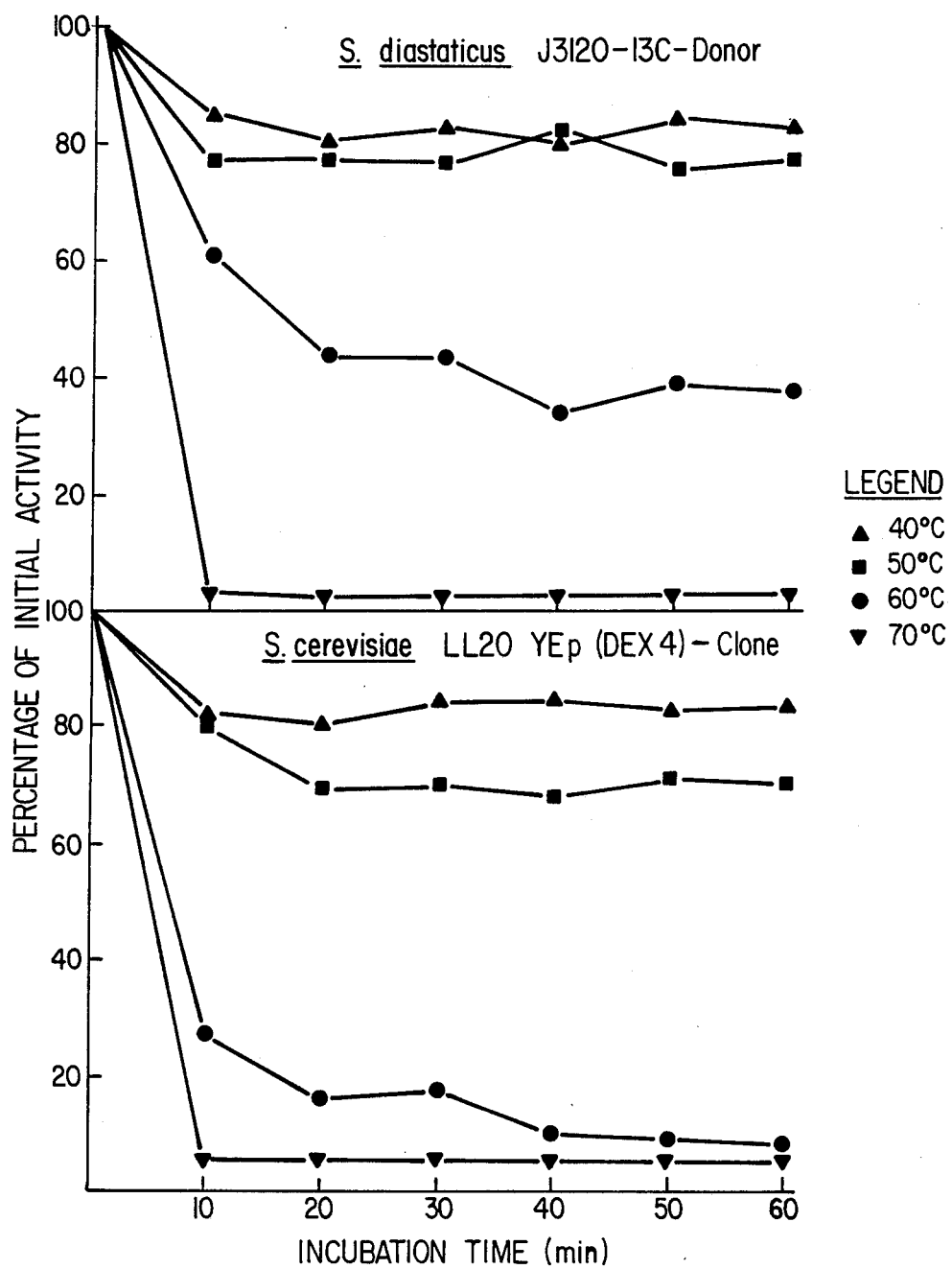
FIG. 4 shows that the glucoamylase, when produced by the transformed S. cerevisiae, is thermolabile when compared to the one produced by S. diastaticus.

[a]Glucoamylase activity is expressed as the amount of glucose (μg/ml) hydrolyzed from 2% dextrin at 25° C. in 1 h, in a cell free system The biochemical characteristics of the glucoamylase produced by the invention should be noted. The pH optimum of the glucoamylase produced by *S. diastaticus* and from a clone containing the plasmid YEp(DEX)4 is the same (about pH 5.0). However, as can be seen from FIG. 3, the temperature optima are different. The temperature optimum of the clone is lower. The temperature stability at high (greater than about 70° C.) temperatures and at low (lower than about 40° C.) temperatures is about the same. However, the cloned glucoamylase is more temperature labile (see FIG. 4) at 50° C. and 60° C. (particularly the latter) than the glucoamylase from *S. diastaticus*. An unexpected point of difference from Yamashita and Fukui (1983 op cit.) and Meaden et al. (1985, op cit.) is that both groups of workers reported no differences in temperature optima.

It is not known what is the cause of these unexpected differences in temperature optima and stability. These may be brought about by among other things changes at the protein level or as a result of post-translational modification, such as glycosylation. However, these differences do produce a glucoamylase with different utility, in that it is thermolabile.

We claim:

1. A method of producing a transformed Saccharomyces yeast containing a gene coding for a glucoamylase, comprising:
   (a) isolating genomic DNA from a strain of *Saccharomyces diastaticus;*
   (b) digesting said genomic DNA with BamHI restriction endonuclease selected to yield DNA fragments containing complete copies of said gene;
   (c) selecting DNA fragments from a sucrose gradient comprising fragments of about 3.9 Kb; and
   (d) ligating the product of step (c) into a Saccharomyces cloning vehicle;
   (e) transforming *E. coli* and the RR1 strain type with the product of step (d);
   (f) isolating in amplified form the product of step (d);
   (g) transforming said Saccharomyces yeast with said amplified cloning vehicle; and
   (h) screening transformants resulting from step (e) for those which express the glucoamylase gene; said glucoamylase gene being contained within a BamHI genomic *Saccharomyces diastaticus* DNA fragment of about 3.9 Kb, said fragment containing no HindIII and no BamHI restriction endonuclease sites and only one PvuII restriction endonuclease site therein.

2. The method of claim 1 wherein the strain of *Saccharomyces diastaticus* is J3120-13C.

3. The method of claim 1 step (d) wherein said cloning vehicle is YEp13.

4. A Saccharomyces cloning vehicle containing a gene coding for a glucoamylase, said glucoamylase gene being contained within a BamHI genomic *Saccharomyces diastaticus* DNA fragment of about 3.9 Kb, said fragment containing no HindIII and no BamHI restriction endonuclease sites and only one PvuII restriction endonuclease site therein.

5. The cloning vehicle of claim 4 wherein the 3.9 Kb BamHI fragment is derived from *Saccharomyces diastaticus* J3120-13C.

6. The cloning vehicle of claim 4 wherein said cloning vehicle is YEp13.

7. A transformed Saccharomyces yeast cell containing a cloning vehicle comprising a gene coding for a glucoamylase, said glucoamylase gene being contained within a BamHI genomic *Saccharomyces diastaticus* DNA fragment of about 3.9 Kb, said fragment containing no HindIII and no BamHI restriction endonuclease sites and only one PvuII restriction endonuclease site therein.

8. The transformed yeast cell of claim 7 wherein the cloning vehicle is YEp13.

9. The transformed yeast cell of claim 7 wherein the gene coding for glucoamylase is derived from *Saccharomyces diastaticus* J3120-13C.

* * * * *

UNITED STATES PATENT AND TRADEMARK OFFICE
CERTIFICATE OF CORRECTION

PATENT NO. : 4,870,014
DATED : 26 September 1989
INVENTOR(S) : Judy A. Erratt & Anwar Nasim It is certified that error appears in the above-identified patent and that said Letters Patent is hereby corrected as shown below:

Cover page, inventors designation below line [19], and line [75], the first inventor's surname is "Erratt"

[57] Abstract, line 1, spelling of "invention" and "glucoamylase" corrected

Column 2, line 52, an open bracket "(" inserted before 'mat a'

Claim 1 (e), should read "E. coli of the RR1 ..."

Signed and Sealed this

Sixteenth Day of October, 1990

Attest:

HARRY F. MANBECK, JR.

Attesting Officer    Commissioner of Patents and Trademarks